(12) United States Patent
Taranta et al.

(10) Patent No.: US 9,968,083 B2
(45) Date of Patent: May 15, 2018

(54) SOLID AGROFORMULATIONS PREPARED FROM A MELT OF PESTICIDE AND POLYALKOXYLATE, OPTIONALLY CONTAINING LIQUID ADJUVANT COMPLEXED WITH POLYCARBOXYLATE

(71) Applicants: Claude Taranta, Stutensee (DE);
Thomas Bork, Westhofen (DE);
Jochen Schreieck, Schifferstadt (DE);
Helmut Müller, Weisenheim (DE);
Nadine Riediger, Schifferstadt (DE);
Clark D. Klein, Pittsboro, NC (US);
Rebecca Willis, Garner, NC (US);
Tatjana Sikuljak, Mannheim (DE);
Murat Mertoglu, Ludwigshafen (DE)

(72) Inventors: Claude Taranta, Stutensee (DE);
Thomas Bork, Westhofen (DE);
Jochen Schreieck, Schifferstadt (DE);
Helmut Müller, Weisenheim (DE);
Nadine Riediger, Schifferstadt (DE);
Clark D. Klein, Pittsboro, NC (US);
Rebecca Willis, Garner, NC (US);
Tatjana Sikuljak, Mannheim (DE);
Murat Mertoglu, Ludwigshafen (DE)

(73) Assignee: BASF SE, Ludwigshafen (DE)

(*) Notice: Subject to any disclaimer, the term of this patent is extended or adjusted under 35 U.S.C. 154(b) by 0 days. days.

(21) Appl. No.: 14/365,421

(22) PCT Filed: Nov. 29, 2012

(86) PCT No.: PCT/EP2012/073986
§ 371 (c)(1),
(2) Date: Jun. 13, 2014

(87) PCT Pub. No.: WO2013/087417
PCT Pub. Date: Jun. 20, 2013

(65) Prior Publication Data
US 2014/0364317 A1    Dec. 11, 2014

Related U.S. Application Data

(60) Provisional application No. 61/570,849, filed on Dec. 15, 2011.

(30) Foreign Application Priority Data

Dec. 22, 2011 (EP) ..................... 11195304

(51) Int. Cl.
*A01N 25/24* (2006.01)
*A01N 25/10* (2006.01)
*A01N 25/12* (2006.01)
*A01N 25/30* (2006.01)
*A01N 43/653* (2006.01)
(Continued)

(52) U.S. Cl.
CPC ............. *A01N 25/24* (2013.01); *A01N 25/10* (2013.01); *A01N 25/12* (2013.01); *A01N 25/30* (2013.01); *A01N 25/32* (2013.01); *A01N 43/56* (2013.01); *A01N 43/653* (2013.01); *A01N 47/20* (2013.01); *A01N 47/24* (2013.01); *A01N 53/00* (2013.01); *A01N 2300/00* (2013.01)

(58) Field of Classification Search
CPC ................................ A01N 25/12; A01N 25/30
USPC .......................................................... 504/360
See application file for complete search history.

(56) References Cited

U.S. PATENT DOCUMENTS

| | | | | |
|---|---|---|---|---|
| 5,474,971 A | * | 12/1995 | Sandell | A01N 25/14 264/211 |
| 5,739,081 A | * | 4/1998 | Lloyd | A01N 25/14 424/405 |

(Continued)

FOREIGN PATENT DOCUMENTS

| | | |
|---|---|---|
| JP | 2279603 | 11/1990 |
| WO | WO 93/25074 | 12/1993 |

(Continued)

OTHER PUBLICATIONS

International Search Report, PCT/EP2012/073986, filed Nov. 29, 2012, report dated Dec. 21, 2012.

(Continued)

*Primary Examiner* — Sreenivasan Padmanabhan
*Assistant Examiner* — Danielle Sullivan
(74) *Attorney, Agent, or Firm* — Brinks Gilson & Lione

(57) ABSTRACT

The present invention relates to a method for a preparation of a solid composition comprising the steps of a) dissolving a premix in a premix-solvent, or melting a premix, wherein the premix contains a pesticide and a nonionic, amphiphilic polyalkoxylate, b) solidifying the premix by removing the premix-solvent, or by cooling, and c) contacting the premix with at least one auxiliary. The invention further relates to a solid composition obtainable by said method; to a method for the preparation of an aqueous tank mix, in which a pesticide is present as suspended particles having a particle size below 1.0 μm, comprising the step of mixing water and a solid composition obtainable by the said method; and to a method for controlling phytopathogenic fungi and/or undesired plant growth and/or undesired attack by insects or mites and/or for regulating the growth of plants, where a solid composition obtainable by said method is allowed to act on the particular pests, their habitat or the plants to be protected from the particular pest, the soil and/or on undesired plants and/or the useful plants and/or their habitat.

12 Claims, No Drawings

(51) Int. Cl.
*A01N 47/24* (2006.01)
*A01N 53/00* (2006.01)
*A01N 25/32* (2006.01)
*A01N 43/56* (2006.01)
*A01N 47/20* (2006.01)

(56) References Cited

U.S. PATENT DOCUMENTS

| | | |
|---|---|---|
| 2004/0013678 A1 | 1/2004 | Schnabel et al. |
| 2007/0066487 A1 | 3/2007 | Schnabel et al. |
| 2009/0170704 A1 | 7/2009 | Kober et al. |
| 2011/0177945 A1 | 7/2011 | Klingelhoefer et al. |
| 2011/0201497 A1 | 8/2011 | Klingelhoefer et al. |

FOREIGN PATENT DOCUMENTS

| | | |
|---|---|---|
| WO | WO 95/18531 | 7/1995 |
| WO | WO 2004006671 | 1/2004 |
| WO | WO 2011/086115 | 7/2011 |
| WO | WO 2011/113786 | 9/2011 |

OTHER PUBLICATIONS

International Preliminary Report on Patentability, PCT/EP2012/073986, filed Nov. 29, 2012, report completed Feb. 4, 2014.

\* cited by examiner

SOLID AGROFORMULATIONS PREPARED FROM A MELT OF PESTICIDE AND POLYALKOXYLATE, OPTIONALLY CONTAINING LIQUID ADJUVANT COMPLEXED WITH POLYCARBOXYLATE

This application is a National Stage application of International Application No. PCT/EP2012/073986, filed Nov. 29, 2012, which claims the benefit of U.S. Provisional Application No. 61/570,849, filed Dec. 15, 2011, the entire contents of which are hereby incorporated herein by reference. This application also claims priority under 35 U.S.C. § 119 to EP Patent Application No. 11195304.8, filed Dec. 22, 2011, the entire contents of which is hereby incorporated herein by reference.

The present invention relates to a method for a preparation of a solid composition comprising the steps of a) dissolving a premix in a premix-solvent, or melting a premix, wherein the premix contains a pesticide and a nonionic, amphiphilic polyalkoxylate, b) solidifying the premix by removing the premix-solvent, or by cooling, and c) contacting the premix with at least one auxiliary. The invention further relates to a solid composition obtainable by said method; to a method for the preparation of an aqueous tank mix, in which a pesticide is present as suspended particles having a particle size below 1.0 µm, comprising the step of mixing water and a solid composition obtainable by the said method; and to a method for controlling phytopathogenic fungi and/or undesired plant growth and/or undesired attack by insects or mites and/or for regulating the growth of plants, where a solid composition obtainable by said method is allowed to act on the particular pests, their habitat or the plants to be protected from the particular pest, the soil and/or on undesired plants and/or the useful plants and/or their habitat. The preferred embodiments of the invention mentioned herein below have to be understood as being preferred either independently from each other or in combination with one another.

Crop protection agents are formulated in solid or liquid compositions, usually in the form of a concentrate for ease of handling and transportation, which is diluted with water by the user before application. Liquid formulations in the form of emulsifiable concentrates contain a very high proportion of organic solvent (often up to 80 percent) which are increasingly coming under scrutiny for their effect on the environment; emulsion concentrates have a higher water content but still contain organic solvents. Suspension concentrates, another water-based liquid form, are often viscous giving rise to handling problems and loss of active ingredient through retention in the packaging. Solid formulations can also have disadvantages; the more common granules and powders in particular can be difficult to measure but more importantly can be dusty and pose inhalation hazards for the formulator and the user. Tablets have not been used extensively because they are often slow to dissolve. In addition, solid formulations have been found generally to possess a lower biological activity than liquid formulations. Also, with unsophisticated mixing techniques at the site of use, usually in a farmer's field, the tendency of solid forms not to disperse immediately can cause not only clogging of spray equipment with undispersed formulation, but also an inadequate application of active ingredient to the crop to be treated. Thus there is a need for a fast-dispersing solid crop protection formulation which has better handling characteristics and enhanced biological activity over conventional forms, to satisfy both environmental concerns and provide an effective, product for the farmer to use in an unsophisticated manner in the field. Object of the present invention was to overcome the above mentioned problems.

The object was solved by a method for the preparation of a solid composition comprising the steps of
a) dissolving a premix in a premix-solvent or melting a premix, wherein the premix contains a pesticide and a nonionic amphiphilic polyalkoxylate,
b) solidifying the premix by removing the premix-solvent or by cooling, and
c) contacting the premix with at least one auxiliary.

The steps a) to c) are usually made in the given order, starting with a), followed by b), and subsequently c).

Solid compositions are usually agrochemical formulations, for example wettable powders or dusts (e.g. WP, SP, WS, DP, DS), pressings (e.g. WT, BR, TB, DT), granules (e.g. WG, SG, GR, FG, GG, MG), and mixtures thereof. Preferably, the solid composition is a pressing or a granule, in particular a granule.

The term pesticides refers to at least one active substance selected from the group of the fungicides, insecticides, nematicides, herbicides, safeners and/or growth regulators. Preferred pesticides are fungicides, insecticides, and herbicides. Mixtures of pesticides of two or more of the abovementioned classes may also be used. The skilled worker is familiar with such pesticides, which can be found, for example, in the Pesticide Manual, 15th Ed. (2009), The British Crop Protection Council, London. Examples of pesticides may be selected from the following list (groups A) to L) are fungicides):

a) Respiration Inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methylacetamide, pyribencarb, triclopyricarb/chlorodincarb, famoxadone, fenamidone;

inhibitors of complex III at Q, site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S, 7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate;

inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)
—C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: imazalil, pefurazoate, prochloraz, triflumizol; pyrimidines, pyridines and piperazines: fenarimol, nuarimol, pyrifenox, triforine;
Delta14-reductase inhibitors: aldimorph, dodemorph, dodemorph-acetate, fenpropimorph, tridemorph, fenpropidin, piperalin, spiroxamine;
Inhibitors of 3-keto reductase: fenhexamid;

C) Nucleic Acid Synthesis Inhibitors
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate, 5-fluorocytosine, 5-fluoro-2-(p-tolylmethoxy) pyrimidin-4-amine, 5-fluoro-2-(4-fluorophenyl-methoxy)pyrimidin-4-amine;

D) Inhibitors of Cell Division and Cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
other cell division inhibitors: diethofencarb, ethaboxam, pencycuron, fluopicolide, zoxamide, metrafenone, pyriofenone;

E) Inhibitors of Amino Acid and Protein Synthesis
methionine synthesis inhibitors (anilino-pyrimidines): cyprodinil, mepanipyrim, pyrimethanil;
protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors
MAP/histidine kinase inhibitors: fluoroimid, iprodione, procymidone, vinclozolin, fenpiclonil, fludioxonil;
G protein inhibitors: quinoxyfen;

G) Lipid and Membrane Synthesis Inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
compounds affecting cell membrane permeability and fatty acids: propamocarb, propamocarb-hydrochlorid H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon;

I) Cell Wall Synthesis Inhibitors
inhibitors of glucan synthesis: validamycin, polyoxin B;
melanin synthesis inhibitors: pyroquilon, tricyclazole, carpropamid, dicyclomet, fenoxanil;

J) Plant Defense Inducers
acibenzolar-5-methyl, probenazole, isotianil, tiadinil, prohexadione-calcium; phosphonates: fosetyl, fosetyl-aluminum, phosphorous acid and its salts;

K) Unknown Mode of Action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropyl-methoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)phenyl)-N-ethyl-N-methyl formamidine, 2-{1-[2-(5-methyl-3-trifluoromethyl-pyrazole-1-yl) acetyl]piperidin-4-yl}-thiazole-4-carboxylic acid methyl-(1,2,3,4-tetrahydro-naphthalen-1-yl)amide, 2-{1-[2-(5-methyl-3-trifluoromethyl-pyrazole-1-yl)-acetyl]piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-methylphenyl)-2,3-dimethyl-isoxazolidin-3-yl]-pyridine, 3-[5-(4-chloro-phenyl)-2,3-dimethyl-isoxazolidin-3-yl]pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), Candicta oleophila 1-82 (e.g. ASPIRE® from Ecogen Inc., USA), *Candida saitoana* (e.g. BIO-CURE® (in mixture with lysozyme) and BIO-COAT® from Micro Flo Company, USA (BASF SE) and Arysta), Chitosan (e.g. ARMOUR-ZEN from BotriZen Ltd., NZ), *Clonostachys rosea f. catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICO-VAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth Regulators
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadionecalcium), prohydrojasmon, thidiazuron, triapenthenol, tributyl phosphorotrithioate, 2,3,5-tri-iodobenzoic acid, trinexapac-ethyl and uniconazole;

N) Herbicides
acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;
aryloxyphenoxypropionates: clodinafop, cyhalofop-butyl, fenoxaprop, fluazifop, haloxyfop, metamifop, propaquizafop, quizalofop, quizalofop-P-tefuryl;
Bipyridyls: diquat, paraquat;
(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones: butroxydim, clethodim, cycloxydim, profoxydim, sethoxydim, tepraloxydim, tralkoxydim;
dinitroanilines: benfluralin, ethalfluralin, oryzalin, pendimethalin, prodiamine, trifluralin;
diphenyl ethers: acifluorfen, aclonifen, bifenox, diclofop, ethoxyfen, fomesafen, lactofen, oxyfluorfen;
hydroxybenzonitriles: bomoxynil, dichlobenil, ioxynil;
imidazolinones: imazamethabenz, imazamox, imazapic, imazapyr, imazaquin, imazethapyr;
phenoxy acetic acids: clomeprop, 2,4-dichlorophenoxyacetic acid (2,4-D), 2,4-DB, dichlorprop, MCPA, MCPA-thioethyl, MCPB, Mecoprop;
pyrazines: chloridazon, flufenpyr-ethyl, fluthiacet, norflurazon, pyridate;
pyridines: aminopyralid, clopyralid, diflufenican, dithiopyr, fluridone, fluoroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;
ureas: chlorotoluron, daimuron, diuron, fluometuron, isoproturon, linuron, methabenzthiazuron, tebuthiuron;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
others: amicarbazone, aminotriazole, anilofos, beflubutamid, benazolin, bencarbazone, benfluresate, benzolenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methylphenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methylparathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alphacypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, pyrifluquinazon, and cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-[2-hydroxy-4,6a,12b-trimethyl-11-oxo-9-(3-pyridinyl)-2H,11H-naphtho[2,1-b]pyrano[3,4-e]pyran-3,6-diyl]ester.

Preferred pesticides are pyraclostrobin, metconazole, alpha-cypermethrin, boscalid, epoxiconazol.

The pesticide is preferably is insoluble in water. For example, the pesticide has a solubility in water of up to 10 WI, preferably up to 2 WI, and in particular up to 0.5 WI, at 20° C.

Suitable nonionic, amphiphilic polyalkoxylate are free of ionic groups. The polyalkoxylate is amphiphilic, which usually means that is has surfactant properties and lowers the surface tension of water. Usually, the polyalkoxylate is obtainable by alkoxylation using alkyleneoxides, such as $C_2$-$C_6$-alkylene oxide, preferably ethylene oxide, propylene oxide, or butylene oxide. Examples of polyalkoxylates are block polymers or compounds such as alcohols, alkylphenols, amines, amides, arylphenols, fatty acids or fatty acid esters which have been alkoxylated with 1 to 50 equivalents.

The polyalkoxylate may have a melting point of at least 35° C., preferably at least 43° C., more preferably at least 48° C. and in particular at least 50° C.

The polyalkoxylate is usually soluble in water at 20° C. Preferably, the solubility in water of the polyalkoxylate is at least 3 wt %, more preferably at least 7 wt %, and in particular at least 10 wt %.

The molecular weight of the polyalkoxylate is usually in the range of from 0.5 to 50 kDa, preferably from 2 to 35 kDa, and in particular from 5 to 20 kDa.

The polyalkoxylate is preferably a block polymer, which may contain a hydrophilic block and a hydrophobic block. Suitable block polymers are block polymers of the A-B or A-B-A type comprising blocks of polyethylene oxide and polypropylene oxide, or of the A-B-C type comprising alkanol, polyethylene oxide and polypropylene oxide.

Preferably, the polyalkoxylate is a block polymer comprising at least one polyethoxylate block and at least one poly-$C_3$-$C_5$-alkoxylate block (e.g. polypropoxylate or polybutoxylate).

In particular, the polyalkoxylate is a triblock polymer of A-B-A type comprising a polyethoxylate type A block and a poly-$C_3$-$C_5$-alkoxylate block (preferably polypropoxylate) type B block.

The solid composition may comprise auxiliaries. Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers, effervescent, and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates;

amines; amides, e.g. N-methylpyrrolidone, fatty acid dimethylamides; and mixtures thereof. Typically, the solid formulations contains up to 10 wt % solvents and liquid carriers (e.g. water), preferably up to 5 wt %, and in particular up to 3 wt %.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, methylcellulose, starch; fertilizers, e.g. ammonium sulfate, ammonium phosphate, ammonium nitrate, ureas; products of vegetable origin, e.g. cereal meal, tree bark meal, wood meal, nutshell meal; sugars, e.g. mono- or disaccharides, and mixtures thereof. Preferred solid carriers are mono- or di-saccharides, polysaccharides, and mixtures thereof. Preferred are water soluble solid carriers, which may have a solubility in water at 20° C. of at least 3 wt %, preferably at least 7 wt %, and in particular at least 10 wt %.

Suitable effervescent is a combination of a hydrogen carbonate and an organic acid, such as a combination of citric acid and potassium hydrogencarbonate. Examples of the hydrogen carbonate include sodium hydrogen carbonate, potassium hydrogen carbonate and ammonium hydrogen carbonate. Examples of the organic acid include citric acid, succinic acid, malic acid, lactic acid, tartaric acid, fumaric acid and maleic acid. The organic acid is preferably used in an amount of 0.5 percent by weight to 20 percent by weight and, particularly, 1 percent by weight to 10 percent by weight based on the whole weight. The organic acid may be used alone or as a mixture of two or more of them. The hydrogencarbonate can be preferably used in an amount of 0.25 times to 2 times by molar ratio of the amount of the organic acid.

Suitable surfactants are surface-active compounds, such as anionic, cationic, nonionic and amphoteric surfactants, polyelectrolytes, and mixtures thereof. Preferred surfactants are anionic surfactants. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Preferred adjuvants are non-ionic surfactants selected from alkoxylates. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. More preferred adjuvants are linear or branched, aliphatic $C_6$-$C_{20}$-alkanols, which have been alkoxylated with ethylene oxide and optionally with propylene oxide.

Suitable thickeners are polysaccharides (e.g. xanthan gum, carboxymethylcellulose), anorganic clays (organically modified or unmodified), polycarboxylate thickeners, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

The solid composition may comprise a polycarboxylate. Usually, polycarboxylates are water-soluble or water-dispersible. Preferred is a polycarboxylate, which is soluble in water, e.g. at least 50 g/l, preferably at least 100 g/l, each at 20° C. Polycarboxylates are polymers, which may comprise carboxylic acid groups in free acid form and/or as salt. More specifically, polycarboxylates are copolymers of ethylenically unsaturated carboxylic acid and/or anhydride.

Preferred polycarboxylates are copolymers of at least one ethylenically unsaturated carboxylic acid and/or anhydride, and of at least one ethylenically unsaturated nonionic monomer. More preferred polycarboxylates are copolymers of an ethylenically unsaturated, linear or branched aliphatic, cycloaliphatic or aromatic monocarboxylic or polycarboxylic acid or anhydride and of alpha-monoolefins containing from 2 to 20 carbon atoms.

Suitable acid or anhydride monomers are those containing from 3 to 10 carbon atoms, preferably those of formula $(R^1)(R^2)C=C(R^3)COOH$, in which $R^1$, $R^2$ and $R^3$ are identical or different and represent a hydrogen atom, a hydrocarbon-based radical containing from 1 to 4 carbon atoms, preferably methyl, a —COOH function, a radical —R—COOH, in which R represents a hydrocarbon-based residue containing from 1 to 4 carbon atoms, preferably an alkylene residue containing 1 or 2 carbon atoms, most particularly methylene. Mixtures of such monomers are also suitable.

Preferentially, at least one of the radicals $R^1$ and $R^2$ is hydrogen. In particular, the acid or anhydride monomers are selected from acrylic, methacrylic, crotonic, maleic, fumaric, citraconic or itaconic acid or anhydride, wherein maleic acid and/or its anhydride are most preferred.

Suitable ethylenically unsaturated nonionic monomers are alpha-monoolefin monomers, such as ethylene, propylene, 1-butene, isobutylene, n-1-pentene, 2-methyl-1-butene, n-1-hexene, 2-methyl-1-pentene, 4-methyl-1-pentene, 2-ethyl-1-butene, diisobutylene (or 2,4,4-trimethyl-1-pentene) and 2-methyl-3,3-dimethyl-1-pentene. Mixtures of such monomers are also suitable.

The molar ratio between the two types of monomer may be in the range from 20/80 to 80/20, preferably from 30/70 to 70/30, and in particular from 40/60 to 60/40. The molecular weight of the polycarboxylate may be 1 to 40 kDa, preferably 2 to 20 kDa, and in particular 3 to 14 kDa.

In a preferred form, the solid composition comprises a solid adjuvant obtainable by dissolving the polycarboxylate and a liquid adjuvant in water, and removing the water.

Suitable liquid adjuvants may be selected from the aforementioned adjuvants. The liquid adjuvant may have a melting point below 30° C., preferably below 10° C. Preferred liquid adjuvants are non-ionic surfactants selected from alkoxylates. Examples of alkoxylates are compounds such as alcohols, which have been alkoxylated with 1 to 30 equivalents. Ethylene oxide and/or propylene oxide may be employed for the alkoxylation, preferably ethylene oxide.

The liquid adjuvant and the polycarboxylate may be dissolved in water at 5 to 100° C. The concentration of the polycarboxylate in water may be from 1 to 50 wt %, preferably from 5 to 40 wt %. The concentration of the liquid adjuvant in water may be from 1 to 50 wt %, preferably from 5 to 40 wt %. The weight ratio of the liquid adjuvant and the polycarboxylate are usually from 8/2 to 2/8, preferably from 7/3 to 3/7. The water may be removed by heating and/or applying reduced pressure.

The solid adjuvant may contain up to 20 wt %, preferably up to 10 wt % water. The solid adjuvant may be broken or milled for further processing. It may be added in step c) for forming the solid composition.

The solid composition (e.g. the granules) may comprise 0.1 to 60 wt %, preferably 0.5 to 40 wt %, and in particular 3 to 20 wt % of the pesticide.

The solid composition (e.g. the granules) may comprise 1 to 60 wt %, preferably 4 to 40 wt %, and in particular 8 to 23 wt % of the polyalkoxylate.

The solid composition (e.g. the granules) may comprise 5 to 60 wt %, preferably 10 to 40 wt %, and in particular 15 to 35 wt % of the anionic surfactant.

The solid composition (e.g. the granules) may comprise 3 to 80 wt %, preferably 7 to 65 wt %, and in particular 10 to 55 wt % of the solid carrier (preferably a water soluble, solid carrier).

The solid composition (e.g. the granules) may comprise at least 3 wt %, preferably at least 5 wt %, and in particular at least 8 wt % of the adjuvant. The solid composition may comprise up to 50 wt %, preferably up to 30 wt % of the adjuvant.

The solid composition (e.g. the granules) may comprise at least 3 wt %, preferably at least 5 wt %, and in particular at least 8 wt % of the polycarboxylate. The solid composition may comprise up to 35 wt %, preferably up to 25 wt % of the polycarboxylate.

The method for the preparation of the solid composition comprises in step a) dissolving a premix in a premix-solvent, or melting a premix, wherein the premix contains a pesticide and a nonionic, amphiphilic polyalkoxylate. Preferably, step a) is melting the premix. In particular, step a) is melting the premix and step b) is solidifying the premix by cooling.

For dissolving the premix in a premix-solvent, any organic solvent (such as water or organic solvent) may be used. Usually, the premix-solvent has a boiling point of up to 200° C., preferably up to 150°, and in particular up to 110° C. Examples for premix-solvents are THF. The pesticide and the polyalkoxylate may be soluble in the premix-solvent.

For melting the premix, which contains the pesticide and the nonionic, amphiphilic polyalkoxylate, the premix may be heated above the melting point of the pesticide, of the polyalkoxylate, or of both. The molten premix may contain the pesticide and/or (preferably and) the polyalkoxylate in liquid form. The premix may be heated to a temperature of at least 30° C., preferably at least 50° C., and in particular at least 60° C. The premix is usually mixed during heating. Preferably, when melting the premix, it contains less than 10 wt %, preferably less than 5 wt %, and in particular less than 2 wt % of water, an organic solvent, or of the premix-solvent.

The premix may contain at least 70 wt %, preferably at least 85 wt %, and in particular at least 95 wt % of the sum of pesticide and polyalkoxylate. The premix may contain up to 20 wt %, preferably up to 10 wt %, and in particular up to 5 wt % of other compounds (e.g. auxiliaries) beside the pesticide and the polyalkoxylate.

The method for the preparation of the solid composition comprises in step b) solidifying the premix by removing the premix-solvent, or by cooling. Preferably, step b) comprises solidifying the premix by cooling. The premix may be cooled below a temperature at which the premix is solid, e.g. below 30° C. The premix-solvent may be removed by heating the premix above the boiling temperature of the premix-solvent, and optionally applying reduced pressure.

Optionally, the solid premix prepared in step b) may be subjected to breaking or milling. The breaking or milling of the solid premix typically results in a particulate premix, having a typical particle size of up to 10 cm, preferably up to 1 mm, and in particular up to 200 µm.

The method for the preparation of the solid composition comprises in step c) contacting the premix with at least one auxiliary. Suitable auxiliaries are given above and may be selected by an expert according to the desired formulation type. The contacting of the premix with at least one auxiliary may be done by conventional means, such as mixing, milling, extruding.

In a preferred form, the solid composition is a tablet, in particular a water dispersible tablet (WT). The tablet may be formed (e.g. in step c)) by compressing of the particulate premix and auxiliaries, such as an effervescent.

In another preferred form, the solid composition is a granule, in particular a water dispersible granule (WG). The granule may be formed (e.g. in step c)) by extrusion of the particulate premix and auxiliaries, such as the solid adjuvant.

The present invention further relates to a solid composition obtainable by (preferably obtained by) the method for a preparation of the solid composition comprising the steps of a) dissolving a premix in a premix-solvent, or melting a premix, wherein the premix contains a pesticide and a nonionic, amphiphilic polyalkoxylate,
b) solidifying the premix by removing the premix-solvent, or by cooling, and
c) contacting the premix with at least one auxiliary.

The present invention further relates to a method for the preparation of an aqueous tank mix, in which a pesticide is present as suspended particles having a particle size below 1.0 μm, comprising the step of mixing water and the solid composition obtainable by (preferably obtained by) the method for a preparation of the solid composition comprising the steps of
a) dissolving a premix in a premix-solvent, or melting a premix, wherein the premix contains a pesticide and a nonionic, amphiphilic polyalkoxylate,
b) solidifying the premix by removing the premix-solvent, or by cooling, and
c) contacting the premix with at least one auxiliary.

The pesticide is preferably present in the tank mix as suspended particles having a particle size below 0.8 μm, and in particular below 0.5 μm. In another form said particle size is in the range from 0.05 to 0.7 μm, preferably from 0.08 to 0.5 μm, and in particular form 0.1 to 0.4 μm.

The mixing of the solid composition and the water may be done directly in a spraying apparatus containing a tank. The mixing may be done at 5 to 50° C., preferably at 10 to 30° C. The mixing may be done by adding the solid composition to the water already present in a tank, and optionally stirring.

The present invention further relates to a method for controlling phytopathogenic fungi and/or undesired plant growth and/or undesired attack by insects or mites and/or for regulating the growth of plants, where the solid composition obtainable by the method according to the invention is allowed to act on the particular pests, their habitat or the plants to be protected from the particular pest, the soil and/or on undesired plants and/or the useful plants and/or their habitat.

When employed in plant protection, the amounts of pesticides (also called active substances) applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

The user applies the solid composition after preparing an aqueous tank mix usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

The present invention has various advantages: The solid composition is easily dispersed in water. The solid composition results after mixing with water in a smaller particle size of the dispersed pesticide compared to known solid compositions. The solid composition has higher biological efficacy, or lower dose rates are required to achieve good pest control. The solid composition is easy to prepare with conventional means, and even liquid adjuvants may be incorporated. The polyalkoxylates are commercially available even in large scale. The polyalkoxylates are very cheap, especially compared to polymers which are used in pharmaceutical industry. The polyalkoxylates are stable towards acids or bases, and do not hydrolyze or crosslink under such conditions. The polyalkoxylates are stable towards higher temperatures, such as above 150° C., and they do not darken or loose their solubility under such conditions. The solid compositions provide at least the same efficacy as liquid adjuvanted compositions, but with lower adjuvant content. The solid composition contain less or no solvents, thus they have a more favourable toxicology profile compared to EC formulations (e.g. a lower worker exposure to solvents). The solid compositions have not stability problems like liquid compositions, such as adjuvanted SC or EC formulations. The solid compositions have not polymorphism problems like SC formulations. The solid compositions are more convenient to handle compared to like liquid compositions.

EXAMPLES

Surfactant 1: naphthalenesulfonic acid-formaldehyde-polycondensate, sodium salt.
Surfactant 2: sodium salt of naphthalene sulfonate condensate.
Surfactant 3: Sodium salt of a sulfated cresol-formaldehyde condensation product.
Defoamer: Silicon based defoamer.
Methylcellulose: water soluble powder of methyl cellulose, Brookfield viscosity about 4000 mPas (20° C., 2 wt %).
Lactose: lactose monohydrate
Stabilizer: organic carboxylic acid, soluble in water (>5 wt %)
Polyalkoxylate A: EO-PO-EO triblockpolymer, Molecular weight about 8000 Da, containing 75-80 wt % EO, >10 wt % water-soluble, melting point about 52°.
Polyalkoxylate B: EO-PO-EO triblockpolymer, Molecular weight 10-15 kDa, containing 70-75 wt % EO; >10 wt % water-soluble, melting point about 55° C.
Adjuvant A: Alkoxylated short fatty alcohol, melting point about 40° C., soluble in water (>5 wt %)
Adjuvant B: Ethoxylated short fatty alcohol, molecular weight about 430 g/mol, soluble in water (>10 wt %).
Adjuvant C: Alkoxylated fatty alcohol, HLB 0.6, mol weight about 900-1000 g/mol.
Adjuvant D: Alkoxylated fatty alcohol, surface tension (EN 14370, 1 g/l dist. water, 23° C.) about 28 mN/m, liquid at room temperature, insoluble in water at 10 wt % at room temperature.
Polycarboxylate A: Aqueous solution (25 wt %) of water soluble sodium salt of copolymer prepared from maleic anhydride and diisobutylene (molar ratio about 1/1), molecular weight about 4-8 kDa.
Polycarboxylate B: Sodium salt of copolymer prepared from maleic acid and diisobutylene, molecular weight about 12 kDa, aqueous solution (25 wt %).
Polycarboxylate C: Sodium salt of copolymer prepared from maleic anhydride and 2,4,4-trimethylpentene, water soluble white powder, Mw about 5 000 g/mol.
Additive A: Kaolinite, powdered.

Example 1

The samples A, B and C were prepared as follows and their composition is summarized in Table 1.

Variant 1: A premix was prepared by heating the pesticide pyraclostrobin, Polyalkoxylate A and/or B, and Stabilizer at 90° C. for one hour until molten. Then the molten premix was cooled to room temperature, and broken into particles.

Variant 2: A premix was prepared by heating the pesticide pyraclostrobin, Polyalkoxylate A and/or B, Stabilizer and tetryhydrofuran (THF) at 90° C. for one hour until a solution was formed. Then the THF was evaporated under reduced pressure and a solid was formed.

The premix of Variant 1 was mixed with Surfactant 1, Surfactant 2, Defoamer, Methylcellulose and Lactose in a kitchen mixer to prepare an extrudable composition. The extrudable composition was added to a low pressure dome extruder and extruded with a sieve of 0.8 mm diameter. The resulting granules were dried at room temperature on a plate.

TABLE 1

Composition of granule formulations (all data in wt %)

|  | A | B | C |
|---|---|---|---|
| Pyraclostrobin | 10 | 10 | 10 |
| Polyalkoxylate A | 14.75 | 0 | 7.38 |
| Polyalkoxylate B | 0 | 14.75 | 7.37 |
| Stabilizer | 0.25 | 0.25 | 0.25 |
| Surfactant 1 | 20 | 20 | 20 |
| Surfactant 2 | 5 | 5 | 5 |
| Defoamer | 1 | 1 | 1 |
| Methylcellulose | 5 | 5 | 5 |
| Lactose | 44 | 44 | 44 |

Example 2

The granules were prepared as described in Example 1 and their final composition is given in Table 2.

TABLE 2

Composition of granule formulations (all data in wt %)

|  | A | B | C |
|---|---|---|---|
| Metconazol | 10 | 10 | 10 |
| Polyalkoxylate A | 15 | 0 | 7.5 |
| Polyalkoxylate B | 0 | 15 | 7.5 |
| Surfactant 1 | 20 | 20 | 20 |
| Surfactant 2 | 5 | 5 | 5 |
| Defoamer | 1 | 1 | 1 |
| Methylcellulose | 5 | 5 | 5 |
| Lactose | 44 | 44 | 44 |

Example 3

The granules were prepared as described in Example 1 and their final composition is given in Table 3.

TABLE 3

Composition of granule formulations (all data in wt %)

|  | A | B | C |
|---|---|---|---|
| Alpha-cypermethrin | 10 | 10 | 10 |
| Polyalkoxylate A | 14.4 | 0 | 7.2 |
| Polyalkoxylate B | 0 | 14.4 | 7.2 |
| Stabilizer | 0.6 | 0.6 | 0.6 |
| Surfactant 1 | 20 | 20 | 20 |
| Surfactant 2 | 5 | 5 | 5 |
| Defoamer | 1 | 1 | 1 |
| Methylcellulose | 5 | 5 | 5 |
| Water | 2 | 2 | 2 |
| Lactose | 42 | 42 | 42 |

Example 4

The biological efficacy was assessed in a preventive trial in a greenhouse, wherein the agro-formulations A, B and C from Example 1 were applied (dose rate 500 ppm or 100 ppm active, spray volume 200 L) to wheat three days before inoculation with *Puccinia recondita* (brown rust). The diseased leaf area was assessed ten days after inoculation and is summarized in Table 4. For comparison, a commercial WG formulation of pyraclostrobin was used (Cabrio EG, BASF Corp.) and named Comparative A.

TABLE 4

Diseased leaf area [%]

| Dose rate | Untreated | A | B | C | Comparative A |
|---|---|---|---|---|---|
| 500 ppm | 70 | 23 | 22 | 37 | 47 |
| 100 ppm | 70 | 40 | 23 | 37 | 47 |

Example 5

The biological efficacy was assessed against southern armyworm 2nd instar larvae, wherein the agroformulations A, B and C from Example 3 were applied (0.25 active/ha). The mean mortality of the larvae was determined 1 to 4 days after treatment (DAT) and is summarized in Table 5. For comparison, a commercial SC formulation of alpha-cypermethrin was used (FASTAC SC, BASF Corp.) and named Comparative B.

TABLE 5

Mean mortality of larvae [%]

|  | 1 DAT | 2 DAT | 3 DAT | 4 DAT |
|---|---|---|---|---|
| Untreated | 0 | 0 | 0 | 0 |
| A | 61 | 83 | 89 | 94 |
| B | 22 | 61 | 67 | 67 |
| C | 33 | 61 | 61 | 61 |
| Comparative B | 0 | 17 | 22 | 22 |

Example 6

The samples A, B and C were prepared as follows and their composition is summarized in Table 6.

Variant 1: A premix was prepared by heating the pesticide pyraclostrobin, Polyalkoxylate A and/or B, and Stabilizer at 90° C. for one hour until molten. Then the molten premix was cooled to room temperature, and broken into particles.

Variant 2: A premix was prepared by heating the pesticide pyraclostrobin, Polyalkoxylate A and/or B, Stabilizer and tetryhydrofuran (THF) at 90° C. for one hour until a solution was formed. Then the THF was evaporated under reduced pressure and a solid was formed.

A solid adjuvant was prepared by dissolving the Adjuvant A (44 wt %) and the Polycarboxylate A (56 wt %) while stirring. The water was removed from this mixture on a plate at 80-90° C. under vacuum. Then the solid mixture was grinded with a mill to a powder.

The premix of Variant 1 was mixed with the solid adjuvant powder, Surfactant 1, Surfactant 2, Defoamer, Methylcellulose and Lactose in a kitchen mixer to prepare an extrudable composition. Optionally 1 wt % water was added to the composition to improve the extrusion. The extrudable composition was added to a low pressure dome extruder and extruded with a sieve of 0.8 mm diameter. The resulting granules were dried at room temperature on a plate.

TABLE 6

Composition of granule formulations (all data in wt %)

|  | A | B | C |
|---|---|---|---|
| Pyraclostrobin | 10 | 10 | 10 |
| Polyalkoxylate A | 14.75 | 0 | 7.38 |
| Polyalkoxylate B | 0 | 14.75 | 7.37 |
| Stabilizer | 0.25 | 0.25 | 0.25 |
| Adjuvant A | 10 | 10 | 10 |
| Polycarboxylate A | 12.5 | 12.5 | 12.5 |
| Surfactant 1 | 20 | 20 | 20 |
| Surfactant 2 | 5 | 5 | 5 |
| Defoamer | 1 | 1 | 1 |
| Methylcellulose | 5 | 5 | 5 |
| Lactose | 21.5 | 21.5 | 21.5 |

Example 7

The granules were prepared as described in Example 6 and their final composition is given in Table 7.

TABLE 7

Composition of granule formulations (all data in wt %)

|  | A | B |
|---|---|---|
| Metconazol | 6 | 6 |
| Polyalkoxylate B | 9 | 9 |
| Adjuvant B | 15 | 20 |
| Polycarboxylate A | 18.75 | 18.75 |
| Surfactant 1 | 20 | 20 |
| Surfactant 2 | 5 | 5 |
| Defoamer | 1 | 1 |
| Methylcellulose | 5 | 5 |
| Lactose | 20.25 | 15.25 |

Example 8

The biological efficacy was assessed as described in Example 4 using the formulations of Example 6. The results are summarized in Table 8.

TABLE 8

Diseased leaf area [%]

| Dose rate | Untreated | A | B | C | Comparative A |
|---|---|---|---|---|---|
| 500 ppm | 70 | 18 | 22 | 18 | 47 |
| 100 ppm | 70 | 27 | 30 | 30 | 47 |

Example 9

The samples A to E were prepared as described in Example 6 and their composition is summarized in Table 9.

TABLE 9

Composition of granule formulations (all data in wt %)

|  | A | B | C | D | E |
|---|---|---|---|---|---|
| Fluxapyroxad | 10 | 10 | 10 | 10 | 10 |
| Adjuvant C | 12.5 | 15 | 12.5 | 12.5 | 9 |
| Adjuvant D |  |  |  |  | 3 |
| Polycarboxylate A | 12.5 |  | 12.5 |  |  |
| Polycarboxylate B |  | 16 |  | 12.5 | 16 |
| Polyalkoxylate B | 15 | 15 | 15 | 15 | 15 |
| Surfactant 2 | 5 | 5 | 5 | 5 | 5 |
| Surfactant 3 | 20 | 20 | 20 | 20 | 20 |
| Methylcellulose | 5 | 5 | 5 | 5 | 5 |
| Defoamer | 1 | 1 | 1 | 1 | 1 |
| Ammonium sulfate |  | 2.5 | 5 |  | 2.5 |
| Additive A |  | 2.5 |  |  | 2.5 |
| Lactose | Ad 100 | Ad 100 | Ad 100 | Ad 100 | Ad 100 |

Example 10

The samples A, B and C were prepared as follows and their composition is summarized in Table 10.

A premix was prepared by heating pyraclostrobin, fluxapyroxad and Polyalkoxylate B at 110° C. for one hour until molten. Then the molten premix was cooled to room temperature, and broken into particles.

A solid adjuvant was prepared by dissolving in the Adjuvant C and/or D (44 wt %) and 25% water solution of the Polycarboxylate C (56 wt %) while stirring. The water was removed from this mixture on a plate at 80-90° C. under vacuum. Then the solid mixture was grinded with a mill to a powder.

The above premix was mixed with the above solid adjuvant powder, Surfactant 2, Surfactant 3, Defoamer, Methylcellulose and Lactose in a kitchen mixer to prepare an extrudable composition. Optionally 1 wt % water was added to the composition to improve the extrusion. The extrudable composition was added to a low pressure dome extruder and extruded with a sieve of 0.8 mm diameter. The resulting granules were dried at room temperature on a plate.

TABLE 10

Composition of granule formulations (all data in wt %)

|  | A | B | C |
|---|---|---|---|
| Fluxapyroxad | 5 | 5 | 5 |
| Pyraclostrobin | 5 | 5 | 5 |
| Adjuvant C | 12.5 | 12.5 | 9 |
| Adjuvant D |  |  | 3 |
| Polycarboxylate C | 12.5 | 16 | 16 |
| Polyalkoxylate B | 15 | 15 | 15 |
| Surfactant 2 | 5 | 5 | 5 |
| Surfactant 3 | 20 | 20 | 20 |
| Methylcellulose | 5 | 5 | 5 |
| Defoamer | 1 | 1 | 1 |
| Lactose | Ad 100 | Ad 100 | Ad 100 |

Example 11

The samples A, B and C were prepared as described in Example 10 and their composition is summarized in Table 11.

TABLE 11

Composition of granule formulations (all data in wt %)

| | A | B | C |
|---|---|---|---|
| Fluxapyroxad | 3.3 | 3.3 | 3.3 |
| Pyraclostrobin | 6.7 | 6.7 | 6.7 |
| Adjuvant C | 12.5 | 12.5 | 9 |
| Adjuvant D | | | 3 |
| Polycarboxylate C | 12.5 | 16 | 16 |
| Polyalkoxylate B | 15 | 15 | 15 |
| Surfactant 2 | 5 | 5 | 5 |
| Surfactant 3 | 20 | 20 | 20 |
| Methylcellulose | 5 | 5 | 5 |
| Defoamer | 1 | 1 | 1 |
| Lactose | Ad 100 | Ad 100 | Ad 100 |

Example 12

The agrochemical formulations were tested in the greenhouse against the fungi *Puccinia triticina* on winter wheat (*Triticum aestivum* cv Monopol). The formulations were mixed with water to yield an aqueous tank mix, which was sprayed at an application rate of 200l/ha. The dose rate of the pesticide or the pesticide mix was 625 ppm fluxapyroxad for samples from Table 9; 1250 ppm fluxapyroxad+pyraclostrobin (Table 10), and 1871 ppm fluxapyroxad+pyraclostrobin (Table 11). The plants were sprayed three days after inoculation (curative treatment). The percentage of infestation was determined and the results were summarized in Tables 12-14.

TABLE 12

Samples from Example 9

| Sample | Infestation [%] |
|---|---|
| Untreated | 80 |
| A | 0 |
| B | 0 |
| C | 1 |
| D | 0 |
| E | 0 |

TABLE 13

Samples from Example 10

| Sample | Infestation [%] At 100% dose rate | Infestation [%] At 20% dose rate |
|---|---|---|
| Untreated | 80 | 80 |
| A | 0 | 15 |
| B | 0 | 13 |
| C | 0 | 13 |

TABLE 14

Samples from Example 11

| Sample | Infestation [%] At 100% dose rate | Infestation [%] At 20% dose rate |
|---|---|---|
| Untreated | 80 | 80 |
| A | 0 | 5 |
| B | 0 | 2 |
| C | 0 | 2 |

The invention claimed is:

1. A method for the preparation of a solid composition comprising the steps of
 a) dissolving a premix in a premix-solvent or melting a premix, wherein the premix contains a pesticide and a nonionic amphiphilic polyalkoxylate, and wherein the molten premix contains the pesticide and the polyalkoxylate in liquid form, and wherein the premix contains up to 20 wt % of other compounds beside the pesticide and the polyalkoxylate;
 b) solidifying the premix by removing the premix-solvent or by cooling,
 c) breaking or milling the solidified premix,
 d) contacting the premix with at least one auxiliary, and
 e) extruding or milling the premix with the added auxiliary,
 wherein the solid composition comprises 1 to 60 wt % of the polyalkoxylate,
 wherein the polyalkoxylate is a block polymer comprising a polyethoxylate block and a poly-$C_3$-$C_5$-alkoxylate block,
 wherein the pesticide is insoluble in water.

2. The method according to claim 1, wherein step a) is melting the premix, and step b) is solidifying the premix by cooling.

3. The method according to claim 1, wherein the solid premix prepared in step b) is subjected to breaking or milling resulting in a particulate premix.

4. The method according to claim 1, wherein the solid composition comprises 5 to 60 wt % of an anionic surfactant.

5. The method according to claim 1, wherein the solid composition comprises a solid adjuvant obtainable by dissolving a polycarboxylate and a liquid adjuvant in water, and removing the water.

6. The method according to claim 1, wherein the solid composition comprises 5 to 40 wt % of the polyalkoxylate.

7. The method according to claim 1, wherein the solid composition comprises 10 to 40 wt % of an anionic surfactant.

8. The method according to claim 1, wherein the solid composition comprises 7 to 65 wt % of a water-soluble, solid carrier.

9. The method according to claim 1, wherein the polyalkoxylate is a triblock polymer of A-B-A type comprising a polyethoxylate type A block and a poly-$C_3$-$C_5$-alkoxylate block type B block.

10. The method of claim 1, wherein the solid composition further comprises a polycarboxylate.

11. The method of claim 8, wherein the solid carrier further comprises a mono- or di-saccharide, polysaccharide or mixtures thereof.

12. The method according to claim 11, wherein the polycarboxylate is a copolymer of at least one ethylenically unsaturated carboxylic acid and/or anhydride, and of at least one ethylenically unsaturated nonionic monomer.

* * * * *